United States Patent [19]

Thompson et al.

[11] Patent Number: 5,187,305

[45] Date of Patent: Feb. 16, 1993

[54] S-NITROSO-N-ALKONOYLPENICILLA-MINES

[75] Inventors: Stephen A. Thompson, Durham; Joel E. Shaffer, Chapel Hill, both of N.C.

[73] Assignee: Glaxo Inc., Research Triangle Park, N.C.

[21] Appl. No.: 617,826

[22] Filed: Nov. 26, 1990

[51] Int. Cl.$^5$ .................. C07C 69/62; C07C 69/66
[52] U.S. Cl. .................. 560/145; 556/413; 556/427
[58] Field of Search ............. 556/413, 422, 427, 437; 560/145; 558/301, 262, 263

[56]  References Cited

U.S. PATENT DOCUMENTS

| | | | |
|---|---|---|---|
| 4,066,689 | 1/1978 | D'Silva | 560/145 X |
| 4,584,014 | 4/1986 | Patterson | 560/145 X |
| 4,927,965 | 5/1990 | Eilon et al. | 560/145 X |
| 4,937,243 | 6/1990 | Markwell et al. | 560/145 X |
| 4,956,181 | 9/1990 | Bayer et al. | 424/448 |
| 4,965,392 | 10/1990 | Fritzberg et al. | 560/145 X |
| 5,093,517 | 3/1992 | Cottman et al. | 560/145 X |

OTHER PUBLICATIONS

J. Pharm. Pharmacol., J. R. Parratt, 31, 801 (1979).
Pharm. Res., L. J. Ignarro, 6, 651 (1989).
Annu. Rev. Physiol., K. E. Kamm, et al., 51, 299 (1989).
The Pharmacological Basis of Therapeutics, A. G. Gilman, et al., 8th Ed., Chap. 32, "Organic Nitrates", pp. 764-774, Pergamon Press, New York (1990).

Primary Examiner—Arthur C. Prescott
Attorney, Agent, or Firm—Charles T. Joyner

[57]  ABSTRACT

The present invention relates to the compounds of formula (I),

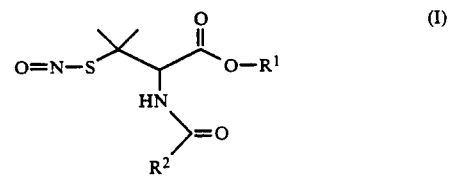

wherein $R^1$ is $C_{1-8}$ alkyl; $C_{5-8}$ cycloalkyl;—$(CH_2)_n$—$Si(CH_3)_3$, wherein n is 1 to 5; $C_{2-5}$ alkylenyl; arylmethylene; aryl; heteroaryl; or wherein such aryl or heteoaryl bears 1 to 3 substituents independently selected from halogen, amino, $C_{1-8}$ alkyl mono- or disubstituted amino, $C_{1-8}$ alkyl and $C_{1-8}$ alkoxy and $R^2$ is $C_{1-8}$ alkoxy, pharmaceutical formulations containing these compounds and their use as vasodilators and in the treatment of cardiovascular disorders.

10 Claims, No Drawings

S-NITROSO-N-ALKONOYLPENICILLAMINES

The present invention relates to novel esters of N-alkanoylcarbonyl-3-(nitrosothio)-valine, also known as S-nitroso-N-alkanoylpenicillamine, especially the phenyl esters of S-nitroso-N-acetyl penicillamine (SNAP) and the use of these compounds in the treatment of cardiovascular disorders.

BACKGROUND OF THE INVENTION

Since the discovery of the vasoactive effects of glyceryl trinitrate (also referred to as nitroglycerin), compounds containing nitrate or nitrite esters groups have been used in the treatment of various cardiovascular disorders such as, angina pectoris, congestive heart failure and myocardial infarction. See Parratt, J. R., J. Pharm. *Pharmacol.*, 31, 801 (1979). The utility of these compounds arises from their ability to release nitric oxide (NO). See Ignarro, L. J., Pharmaceutical Research 6, 651 (1989). NO is believed to activate a soluble form of guanylate cyclase, a cellular enzyme, which catalyses the formation of 3',5' cyclic guanosine monophosphate (cGMP). See Kamm, et al., *Annu. Rev. Physiol.*, 51, 299 (1989). It is the action of cGMP on other cellular targets that is thought to mediate relaxation of vascular smooth muscle and provide the therapeutic effect of nitrovasodilators.

A problem with the use of nitrovasodilators is their tendency to produce "tolerance." See Katz, R. J., *Cardiovascular Drugs and therapy*, 4, 247 (1990). Ignarro, L. J., et al., (*J. Pharmacol. Exp. Ther.*, 218, 739 (1981)) have suggested this tolerance effect results from depletion of intracellular sulfhydrals, such as glutathione, which are essential in the metabolism of nitrovasodilators to NO.

Tolerance of N-acetyl-3-(nitrosothio)-D-valine, also known as S-nitroso-N-acetylpenicillamine (SNAP), is much less of a problem than tolerance of gyceryl trinitrate, and SNAP is one of the most stable nitrosothiols known (see Field, L., et al., *J.C.S. Chem. Commun.*, 249(1978)). SNAP would be an especially useful drug if it could be delivered in such manner as vasodilating organic nitrates and nitrites currently in clinical use, i.e., orally (including sublingually), rectally, vaginally, nasally or transdermally. However, it is poorly absorbed by these routes.

It has now been found that certain novel ester derivatives of SNAP i.e., the compounds of the present invention, are active as low tolerance producing vasodilators, and are much better absorbed through the skin and mucous membranes than SNAP itself. Therefore, these derivatives are suited for oral, rectal, vaginal, nasal and transdermal applications. Some of the compounds of this invention are more potent vasodilators than SNAP and are comparable in this activity to gyceryl trinitrate.

SUMMARY OF THE INVENTION

The present invention relates to the compounds of formula (I).

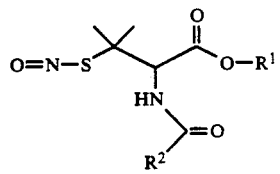

(I)

wherein $R^1$ is $C_{1-8}$ alkyl; $C_{5-8}$ cycloalkyl; —$(CH_2)_n$—$Si(CH_3)_3$, wherein n is 1 to 5; $C_{2-5}$ alkylenyl; arylmethylene; aryl; heteroaryl; or wherein such aryl or heteroaryl bears 1 to 3 substituents independently selected from halogen, amino, $C_{1-8}$ alkyl mono- or disubstituted amino, $C_{1-8}$ alkyl and $C_{1-8}$ alkoxy and $R^2$ is $C_{1-8}$ alkyl or $C_{1-8}$ alkoxy, pharmaceutical formulations containing these compounds and their use as vasodilators and in the treatment of cardiovascular disorders.

The preferred compounds of formula (I) are those wherein $R^1$ is phenyl; or phenyl substituted by halogen, $C_{1-8}$ alkyl or $C_{1-8}$ alkoxy. Especially preferred are the phenyl and substituted phenyl esters of N-acetyl-3-(nitrosothio)-D-valine (SNAP). That is, the compounds of formula (I) wherein $R^1$ is phenyl; or halogen, $C_{1-8}$ alkyl or $C_{1-8}$ alkoxy substituted phenyl and $R^2$ is methyl which have vasodilating properties significantly superior to the free acid form of SNAP and comparable to nitroglycerin based on animal test data.

Specific preferred compounds of formula (I) are:
N-acetyl-3-(nitrosothio)-D-valine phenyl ester and
N-acetyl-3-(nitrosothio)-D-valine 4-methoxyphenyl ester.

Other specific compounds of formula (I) are:
N-acetyl-3-(nitrosothio)-D-valine n-butyl ester,
N-acetyl-3-(nitrosothio)-D-valine t-butyl ester,
N-acetyl-3-(nitrosothio)-D-valine n-octyl ester,
N-acetyl-3-(nitrosothio)-D-valine 2-trimethylsilyethyl ester,
N-acetyl-3-(nitrosothio)-D-valine cyclohexyl ester and
N-acetyl-3-(nitrosothio)-D-valine methyl ester.

In addition, the following compounds of formula (I) may be obtained from the synthetic procedures described herein.
N-n-butyryl-3-(nitrosothio)-D-valine benzyl ester,
N-acetyl-3-(nitrosothio)-L-valine 3-chlorophenyl ester
N-propionyl-3-(nitrosothio)-L-valine 4-N,N-dimethylaminophenyl ester
N-(t-butoxycarbonyl)-3-(nitrosothio)-D-valine 4-methylphenyl ester
N-(ethylcarbonyl)-3-(nitrosothio)-D-valine 3-butenyl ester.

DETAILED DESCRIPTION OF THE INVENTION

In particular for the compound of Formula (I) $R^1$ is $C_{1-8}$ alkyl, e.g., methyl, butyl and octyl; $C_{5-8}$ cycloalkyl, e.g., cyclopentyl and cyclohexyl; —$(CH_2)_n$—$Si(CH_3)_3$, wherein n is 1 to 5; $C_{2-5}$ alkylenyl, e.g., —$CH_2$—$CH=CH_2$ and —$(CH_2)_2CH=CHCH_3$; benzyl; aryl, e.g., phenyl or naphthyl; heteroaryl, e.g. a 5, 6 or 7 member ring interrupted by one or more N, S or O heteroatoms, such as pyrrolyl, imidazolyl, furyl, thienyl, pyridazinyl, pyridyl, pyrimidinyl and pyrazinyl (preferably no two O or S atoms are adjacent in said heteroaryl) or aryl (preferably phenyl) or heteroaryl bearing 1 to 3 substituents selected from halogen (e.g. chloro or bromo), amino, $C_{1-8}$ alkyl mono- or disubstituted amino (e.g., —$NHCH_3$, —$NHCH_2CH_3$ and —$N(CH_3)_2$), $C_{1-8}$ alkyl (e.g., methyl, ethyl, propyl and butyl); $C_{1-8}$ alkoxy (e.g. methoxy, ethoxy, propoxy and butoxy) and $R^2$ is $C_{1-8}$ alkyl, e.g., lower $C_{1-4}$ alkyl, such as methyl, ethyl and butyl, and octyl or $C_{1-8}$ alkoxy, (e.g., lower $C_{1-4}$ alkoxy, such as methoxy, ethoxy, propoxy and butyl and hexoxy).

The compounds of formula (I) may be prepared by reacting a compound of formula (VII) with a reagent capable of introducing the group-N=O as shown in step 6 of Scheme 1. Suitable nitrosating reagents include alkyl nitrites such as t-butyl nitrite. The nitrosation reaction is preferably carried out in a suitable solvent. Thus for example if the nitrosation is carried out using an alkyl nitrite then the reaction is conveniently carried out in an inert solvent such as methylene chloride.

The compounds of formula (VII) may be prepared by any suitable means in the art for preparing esters of carboxylic acids. However, it will be appreciated that prior to an esterification reaction the reactive amino and sulfhydryl groups will usually need to be protected before and deprotected after the esterification. One method is shown in Scheme 1:

In step 4, the blocking groups are removed, e.g., if the blocking group was t-butylcarbonyl, removal may be accomplished by treatment with trifluoroacetic acid, or similar strong organic acid, in a suitable solvent system, e.g., methylene chloride in the presence of anisole. The resulting compound of formula (VI), wherein $X^-$ is an acid anion, is treated in step 5 with a suitable alkanolating agent, e.g., acetyl chloride, or suitable alkylcarbonylating agent, e.g., di-t-butyl dicarbonate, diethyl carbonate or ethyl chloroformate, to yield a compound of formula (VII). Finally in step 6 a compound of formula (I) is produced by treatment of a compound of formula (VII) with a suitable nitrosolating agent e.g., t-butyl nitrite in methylene chloride.

The compounds of formula (I) wherein $R^1$ is $C_{1-8}$ alkyl and $R^2$ is methyl may be prepared by a more direct route as shown in Scheme 2.

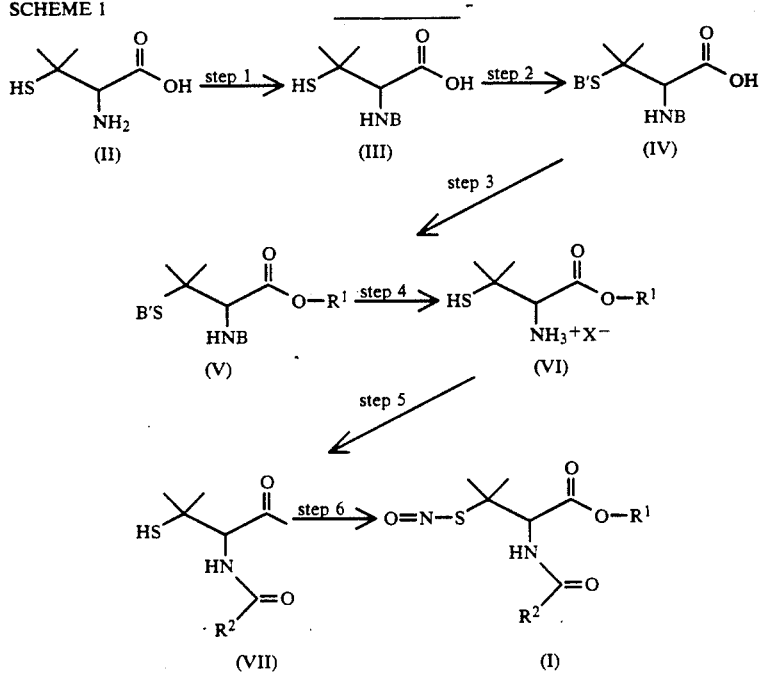

SCHEME 1

In Scheme 1 commercially available penicillamine (also known as 3-thiovaline), the compound of formula (II), is reacted with an amino group protecting (also know as "blocking") agent, e.g., di-t-butyl dicarbonate in a basic medium, in step 1 to yield a compound of formula (III) in which the amino group is "protected" or "blocked" from reacting in subsequent steps. A compound of formula (III) is then reacted with a base, e.g., sodium hydride in tertrahydrofuran, followed by treatment with a suitable sulfhydryl group blocking agent, e.g., di-t-butyl dicarbonate, as shown in step 2 to yield a compound of formula (IV). In formula (IV) the blocking groups, B and B', are independently chosen and may be different from each other. With both the amino and sulfhydryl functional groups blocked, a compound of formula (IV) can be reacted in step 3 with an appropriate $R^1$—OH compound (wherein $R^1$ is as defined for the compounds of formula (I)), e.g., alcohol or phenol, under conditions known in the art, e.g., in the presence of a coupling agent such as benzotriazol-1-yloxytris(-dimethylamino)-phosphium hexafluorophosphate, to produce the esters of formula (V). In formulas (V), (VI) and (VII), $R^1$ is as defined for formula (I), and in formula (VII), $R^2$ is as defined for formula (I).

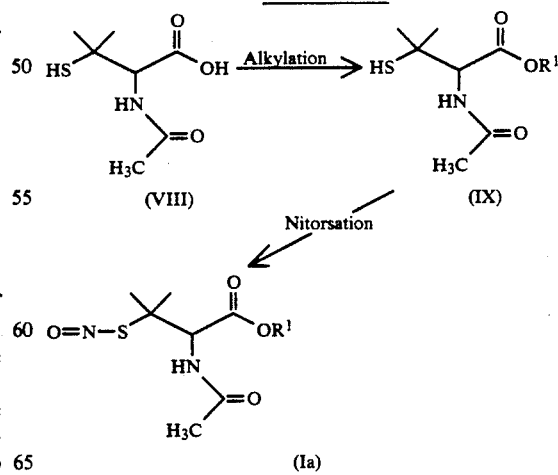

SCHEME 2

Commercially available N-acetyl-penicillamine (VIII) is treated with a $(C_{1-8})$alkyl-N,N-dialkylpseudourea in a suitable inert solvent, e.g., n-butyl-N,N-diisopropyl-pseudourea in dioxane, at ambient to reflux temperatures, to yield a compound of formula (IX) where $R^1$ is $C_{1-8}$ alkyl. In the final step a corresponding compound of formula (I), that is, a compound of formula (Ia), is produced by treatment of a compound of formula (IX) with a suitable nitrosating agent, e.g., t-butyl nitrite in methylene chloride.

Those skilled in the art will appreciated that the compounds of formulas (I) through (IX) have an asymetric carbon adjacent to the carbonyl and amino functions, i.e., the $\alpha$ carbon, and therefore, can exist as at least two stereoisomers. Either stereoisomer may be obtain by starting with penicillamine of the corresponding configuration, i.e., D or L. For simplicity no specific stereoisomer is depicted in the structural drawings herein, but it is to be understood that both the D and L configurations of the compounds of formula (I) at the $\alpha$ carbon and elsewhere in the molecule are within the scope of the invention.

The compounds of formula (I) may be used for the same disorders and administered by the same routes as the nitrovasodilators now in clinical use, i.e., glyceryl trinitrate and erythrityl tetranitrate. For example, chronic myocardial ischemia, congestive heart failure and angina pectoris, may be treated sublingually, orally, rectally, vaginally, transdermally, parenterally or by inhalation. Other conditions in which the compounds formula (I) have utility include the treatment of Prinzmetal's angina, essential hypertension and pulmonary hypertension. The preferred compounds of this invention are particularly suited to transdermal applications.

The amount of active compound, i.e., a compound of formula (I), required for treating the above conditions will vary with the particular compound chosen, the route of administration and the condition of the patient undergoing the treatment, and is ultimately at the discretion of the physician. However, a suitable oral, sublingual or inhalation dose for a mammal, including a human, is in the range of from about 0.01 mg to about 1.5 mg per kilogram body weight per day. For example, a typical dose for a human patient (about 60 to 80 kg) is about 0.6 mg to about 120 mg per day; preferably 30 to 80 mg per day.

The desired daily oral, sublingual or inhalation dose is preferably presented as one to about six sub-doses administered at appropriate intervals throughout the day as needed. A sublingual sub-dose is preferably in the form of a tablet containing about 5 to 10 mg of active compound although other sublingual dosing media known in the art of pharmacy may be employed, e.g., sublingual aerosols. An oral sub-dose of about 5 to 10 mg of active compound may be in the form of a tablet, capsule, syrup, lozenge, suspension or other oral formulation known in the art. Multi-dose pressurized or dry powder dispensers are preferred for inhalation with each sub-dose being about 5 to about 10 mg of active compound.

The compounds of formula (I) may advantageously be administered transdermally to patients who require a small, but continuous dose. The total transdermal dose is about 0.1 to 3.0 mg/kg per day delivered at a uniform rate.

The compounds of formula (I) may be delivered by rectal or vaginal suppository. The total dose per day administered by this route is about 0.1 to 3.0 mg/kg.

Administration of the compounds of formula (I) may also be by a parenteral route such as injection or infusion. This route of administration is particularly useful when other routes are impractical. The infusion dose is about 0.001 to about 0.1 mg/kg per min, and the injection dose is about 0.01 to about 1.0 mg/kg per day given one to four injections per day.

While it is possible for the active compound, i.e., a compound of formula (I) to be administered alone, preferably it is presented in a pharmaceutical formulation. Formulations of the present invention, for medical use, comprise an active compound together with a pharmaceutically acceptable carrier and optionally other therapeutically active ingredients. The carrier should be pharmaceutically acceptable in the sense of being compatible with the other ingredients of the formulation and not deleterious to the recipient thereof.

The present invention, therefore, further provides pharmaceutical formulations each comprising a compound of formula (I) together with a pharmaceutically acceptable carrier therefor.

The formulations include those suitable for oral (including sublingual), transdermal, buccal, nasal, vaginal, rectal or parenteral (including subcutaneous, intramuscular and intravenous) administration. Preferred routes of administration are oral and transdermal.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations for transdermal application may be prepared, for example, by mixing the active compound with a collodial, silicone dioxide suspension and this suspension is sealed between two layers of polymeric laminate to form a thin "sandwich" transdermal system. The side which is in contact with the skin is made of a permeable polymer and its characteristics as a membrane control the release of the drug. The side faceing away from the skin is a nonpermeable polymer. The permeable side is kept in contact with the skin by means of an adhesive or bandage.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compressing or molding the active compound, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent.

For administration by inhalation or sublingual aerosol, the compounds of formula (I) are conveniently delivered in the form of an aerosol spray presentation from multi-dose pressurized packs, with a suitable propellant or, for inhalation, from a nebulizer. In the case of a pressurized aerosol, the dosage unit may be determined by a metering valve.

Alternatively, for administration by inhalation or insufflation, the compounds of formula (I) may take the form of a dry powder composition, e.g., a powder mixture of the compound of formula (I) an a suitable powder base e.g., lactose or starch. The powder composition may be presented in unit dosage.

A syrup may be made by adding the active compound to a concentrated, aqueous solution of a sugar, for example sucrose, to which may also be added any accessory ingredients. Such accessory ingredient(s) may include flavoring, an agent to retard crystallization of the sugar or an agent to increase the solubility of any other ingredient, such as a polyhydric alcohol for example glycerol or sorbitol.

Formulations for rectal or vaginal administration may be presented as a suppository with a conventional carrier such as cocoa butter or WITEPSOL S55 (trademark of Dynamit Nobel, Germany, for a suppository base of glyceryl esters of saturated fatty acids).

Formulations suitable for parenteral administration conveniently comprise a sterile aqueous preparation of the active compound which is preferably isotonic with the blood of the recipient. Such formulations suitably comprise a solution of the active compound which is isotonic with the blood of the recipient. Thus, such formulations may conveniently contain distilled water, 5% dextrose in distilled water or saline and a compound of the formula (I). Useful formulations also comprise concentrated solutions or solids containing an active compound which upon dilution with an appropriate solvent give a solution suitable for parental administration above.

In addition to the aforementioned ingredients, the formulations of this invention may further include one or more optional ingredient(s) utilized in the art of pharmaceutical formulating, e.g. diluents, buffers, flavoring agents, binders, surface active agents, thickeners, lubricants, preservatives (including antioxidants) and the like.

Also part of the invention are the following:

1) The novel compounds of formula (Va),

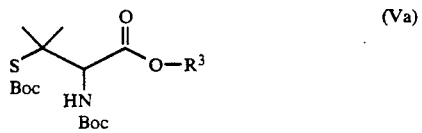

(Va)

wherein Boc is t-butoxycarbonyl and $R^3$ is phenyl or phenyl bearing 1 to 3 substituents independently selected from halogen, amino, $C_{1-8}$ alkyl mono- or disubstituted amino, $C_{1-8}$ alkyl and $C_{1-8}$ alkoxy, are useful in the preparation of compounds of formula (I). Specific compounds of formula (Va) are:
N-(t-butoxycarbonyl)-3-(t-butoxycarbonylthio)-D-valine phenyl ester and
N-(t-butoxycarbonyl)-3-(t-butoxycarbonylthio)-D-valine-4-methoxyphenyl ester.

2) The novel compounds of formula (VIa),

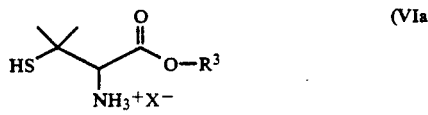

(VIa)

wherein $R^3$ is as defined for formula (Va) and $X^-$ is an acid anion, are useful in the preparation of compounds of formula (I). Specific compound of formular (VI) are:
3-mercapto-D-valine phenyl ester trifluoroacetate and 3-mercapto-D-valine 4-methoxyphenyl ester trifluoroacetate.

3) The novel compounds of formula (VIIa)

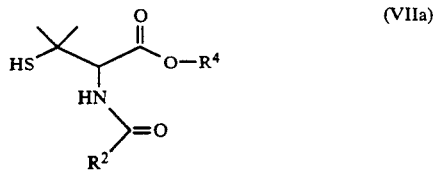

(VIIa)

wherein $R^4$ is butyl, phenyl, or phenyl bearing 1 to 3 substitutents independently selected from halogen, amino, $C_{1-8}$ alkyl mono-or disubstituted amino, $C_{1-8}$ alkyl and $C_{1-8}$ alkoxy, and $R^2$ is $C_{1-8}$ alkyl or $C_{1-8}$ alkoxy are useful in the preparation of compounds of formula (I). Specific compound of formular (VIIa) are:
N-acetyl-3-mercapto-D-valine n-butyl ester,
N-acetyl-3-mercapto-D-valine phenyl ester and
N-acetyl-3-mercapto-D-valine 4-methoxyphenyl ester.

4) The novel compound N-(t-butoxycarbonyl)-3-(t-butoxycarbonylthio)-D-valine is useful in the preparation of compounds of formula (I).

EXAMPLES

The following examples illustrate aspects of this invention but should not be construed as limitations thereto. As used herein the symbols and conventions used in these examples are consistent with those used in the contemporary scientific literature, for example, the *Journal of the American Chemical Society.*

EXAMPLE 1

Aorta Vasodilation Assay

The thoracic aortas removed from euthanized male Sprague-Dawley rats (200–300 g) and male New Zealand, white rabbits (1.5–3.0 kg) are cleaned of adherent connective tissue and cut into rings 3 to 5 mm in length. Endothelium is removed by rolling the rings on moist filter paper. Rings are suspended in an organ chamber containing a physiological salt solution of (mM): NaCl, 118.4; KCl, 4.7; $MgSO_4.H_2O$, 1.2; $CaCl_2.2H_2O$, 2.5; $KH_2PO_4$, 1.2; $NaHCO_3$, 25.0; and dextrose, 11.1. The bathing solution is maintained at 37° C. and half of the tissues are aerated with 95% $O_2$/5% $CO_2$ and half are aerated with 20% $O_2$/5% $CO_2$/75% $N_2$. Tissues are mounted to isometric force displacement transducers and responses are recorded on a polygraph.

All rings are gradually stretched (over a 120 min. period) to a basal resting tension of 2 g (rat) and 4 g (rabbit), which is maintained throughout the assay. During the basal tension adjustment period, the rings are exposed to KCl (40 mM) two to three times to verify tissue contractility. During this period, the effectiveness of endothelium removal is confirmed by the absence of the characteristic relaxation seen with acetylcholine $(1 \times 10^{-6}M)$ in endothelium-intact (but not endothelium-removed) rings contracted with phenylephrine $(1 \times 10^{-7}M)$.

Methylene blue $(1 \times 10^{-5}M)$ is added to half of the tissues aerated at 20% $O_2$ and 95% $O_2$ to inhibit basal cGMP accumulation. Phenylephrine $(1 \times 10^{-7}M)$ is then added and the rings are allowed to obtain a stable contractile response after which time, SOD (100 U/mL) is added to the tissues. The test compound is then added in a cumulative fashion. After the stabilization of the response to the last concentration of the test compound, sodium nitroprusside ($1 \times 10^{-4}$M) is added to induce complete relaxation. Table 1 shows the relaxation induced by each test compound expressed as IC$_{50}$ (20% O$_2$, without methylene blue condition) and as relative potency compared with the standard vasodilator, nitroprusside.

TABLE 1
VASODILATION ASSAY
20% O$_2$, without methylene blue

| COMPOUND | RAT AORTA | | RABBIT AORTA | |
|---|---|---|---|---|
| | IC$_{50}$ μM | RELATIVE POTENCY | IC$_{50}$ μM | RELATIVE POTENCY |
| NITROPRUSSIDE | 0.0025 | 1.00 | 0.02 | 1.00 |
| (I), R$^1$ = PHENYL R$^2$ = METHYL | 0.0076 | 3.04 | 0.065 | 3.25 |
| NITROGLYCERIN | 0.0094 | 3.76 | 0.023 | 1.15 |
| SNAP | 0.14 | 56 | 0.16 | 8.0 |

Relative Potency = $\frac{\text{Test Compound IC}_{50}}{\text{Nitroprusside IC}_{50}}$

EXAMPLE 2

Pharmaceutical formulations (A) Transdermal System

| Ingredients | Amount |
|---|---|
| Active compound | 25.0 mg |
| Silicone fluid | 450.0 mg |
| Colloidal silicone dioxide | 25.0 mg |

The silicone fluid and active compound are mixed together and the colloidal silicone dioxide is added to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene), polyvinyl acetate or polyurethane, and an impermeable backing membrane made of a polyester multilaminate. The system described is a 10 sq. cm patch.

(B) Sublingual Tablet

| Ingredients | Amount |
|---|---|
| Active compound | 5.0 mg |
| Stach | 10.0 mg |
| Magnesium Stearate | 1.0 mg |
| Sodium Saccharin | 10.0 mg |
| Flavoring agent | q.s. |

The active compound, starch and sodium saccharin are granulated with water and dried. Magnesium stearate is added to the dried granules and the mixture is thoroughly blended. The blended mixture is compressed into a tablet.

(C) Sublingual Aerosol

| Ingredients | Amount |
|---|---|
| Active compound | 1.0 mg |
| Propellant 12 (Cl$_2$F$_2$C) | 10.0 g |
| Oleic acid | 8.0 mg |
| Flavoring agent | q.s. |

A suspension is formed by mixing active compound with the propellant, oleic acid and flavor in a pressurized vessel equipped with internal mixing. Contents are charged into a metered dose dispenser using a pressure fill technique and then crimped. A metering valve is chosen so that each dose delivers substantially 5.0 mg of active compound.

(D) Suppository

| Ingredients | Amount |
|---|---|
| Active compound | 25.0 mg |
| Theobromine sodium salicylate | 250.0 mg |
| Witepsol S55 | 1725.0 mg |

The inactive ingredients are mixed and melted. The active compound is then distributed in the molten mixture, poured into molds and allowed to cool.

EXAMPLE 3

N-Acetyl-3-(nitrosothio)-D-valine phenyl ester
(Formula (I), R$^1$=C$_6$H$_5$, R$^2$=CH$_3$)

(A) N-(t-Butoxycarbonyl)-3-mercapto-D-valine. A mixture of D-penicillamine (5.00 g, 33.51 mmol), t-butyl alcohol (100 mL), 2N aqueous sodium hydroxide (25 mL) and di-t-butyl dicarbonate (8.05 g, 36.86 mmol) is stirred at room for about 16 hours. The reaction mixture is diluted with 800 mL of ethyl acetate, and washed with 200 mL of aqueous 3N sodium bisulfate, dried over magnesium sulfate and then concentrated to give 8.21 g of the title compound as a white solid, 98% yield, m.p. 120° C. (decomposes). $^1$H NMR (300 MHz, CDCl$_3$): 5.47 (br d, J=9.3, 1H), 4.30 (d, J=9.3, 1H), 2.02 (s, 1H), 1.54 (s, 3H), 1.44 (s, 9H), 1.40 (s, 3H).

(B) N-(t-Butoxycarbonyl)-3-(t-butoxycarbonylthio)-D-valine. To a solution of the product of Example 3(A) (1.00 g, 4.0 mmol) in 50 mL of anhydrous tetrahydrofuran is added sodium hydride (216 mg, 9.0 mmol) in three portions. The mixture is stirred at room temperature for about an hour, and then di-t-butyl dicarbonate (1.313 g, 6.0 mmol) is added. The mixture is stirred at room temperature for about 16 hours and then poured into 100 ml of saturated aqueous sodium bicarbonate, washed with ethyl acetate, and the pH is adjusted to approximately 2 by adding solid sodium bisulfate. The aqueous phase is then extracted (4×) with methylene chloride. The combined organic phases are dried over magnesium sulfate and concentrated to give 1.11 g of the title compound, 79% yield. $^1$H NMR (300 MHz, CDCl$_3$): 5.73 (d, J=9.5, 1H), 4.74 (d, J=9.5, 1H), 1.53 (s, 3H), 1.52 (s, 3H), 1.47 (s, 9H), 1.43 (s, 9H).

(C) N-(t-Butoxycarbonyl)-3-(t-butoxycarbonylthio)-D-valine phenyl ester.

To a solution of the product of Example 3(B) (720 mg, 2.060 mmol) in 25 mL of methylene chloride is added phenol (1.94 mg, 2.060 mmol), triethylamine (416 mg, 4.121 mmol), and benzotriazol-1-yloxytris (dimethylamino)phosphium hexafluorophosphate (911 mg, 2.060 mmol). The mixture is stirred at room temperature for about 3 hours, then poured into 40 mL of brine, and extracted (3×) with ethyl acetate. The combined organics are washed with 1N hydrochloric acid, saturated sodium bicarbonate, and brine. After drying over magnesium sulfate, the mixture is concentrated and the residue is chromatographed on silica gel (95/5 hexanes/ethyl acetate) to give the compound of formula (V) where, R$^1$=phenyl as an oil: 667 mg, 76% yield. $^1$H NMR (300 MHz, CDCl$_3$): 7.41–7.35 (m, 2H), 7.25–7.14 (m, 3H), 5.73 (d, J=9.5, 1H), 5.07 (d, J=9.5, 1H), 1.63 (s, 3H), 1.56 (s, 3H), 1.47 (s, 18H).

(D) 3-Mercapto-D-Valine phenyl ester trifluoroacetate. To a solution of the product of Example 3(C) (660 mg, 1.551 mmol) in 4 mL of methylene chloride is added 2 mL of anhydrous anisole, and 4 mL of trifluoroacetic acid. After stirring for about 2 hours, and the mixture is concentrated to give the title compound as an off white solid, 522 mg, 99% yield, m.p. 166°–168° C.

(E) N-Acetyl-3-mercapto-D-valine phenyl ester. A solution of the product of Example 3(D) (225 mg, 0.663 mmol) in 10 mL of methylene chloride, and triethylamine (140 mg, 1.392 mmol) is cooled on ice. To this mixture is added acetyl chloride (52 mg, 0.663 mmol) dropwise over about 4 minutes. After stirring for about 15 minutes the mixture is poured into 15 mL of water and extracted with methylene chloride (25 mL). The organic phase is washed with 1N hydrochloric acid (15 mL), water (15 mL), dried over magnesium sulfate and concentrated. The residue is chromatographed on silica gel (3/1 hexanes/ethyl acetate) to give the compound of formula (VII) where R$^1$=phenyl, R$^2$=CH$_3$, as an oil: 102 mg, 57% yield. $^1$H NMR (300 MHz, CDCl$_3$): 7.38–7.08 (m, 5H), 6.43 (br d, J=9.0, 1H), 4.85 (d, J=9.0, 1H), 2.10 (s, 3H), 2.03 (s, 1H), 1.66 (s, 3H), 1.44 (s, 3H).

(F) N-Acetyl-3-(nitrosothio)-D-valine phenyl ester. To a ice cold solution of the product of Example 3(E) (100 mg, 0.374 mmol) in 5 mL of methylene chloride is added t-butyl nitrite (270 mg, 2.62 mmol). After stirring for about 1 hour the mixture is concentrated. The residue is chromatographed on silica gel (3/1 hexanes/ethyl acetate) to give N-acetyl-3-(nitrosothio)-D-valine phenyl ester as a green gum: 98 mg, 88% yield. $^1$H NMR (300 MHz, CDCl$_3$): 7.40–7.12 (m, 4H), 7.00 (d, J=7.3, 1H), 6.36 (br d, J=9.5, 1H), 5.57 (d, J=9.5, 1H), 2.21 (s, 3H), 2.07 (s, 3H), 2.04 (s, 3H).

EXAMPLE 4

N-Acetyl-3-(nitrosothio)-D-valine 4-methoxyphenyl ester (Formula (I), R$^1$=p-CH$_3$OC$_6$H$_4$, R$^2$=CH$_3$)

(A) N-(t-Butoxycarbonyl)-3-(t-butoxycarbonylthio)-D-valine 4-methoxyphenyl ester. To a solution of the product of Example 3(B) (505 mg, 1.445 mmol) in 25 mL of methylene chloride is added 4-methoxyphenol (179 mg, 1.445 mmol), triethylamine (292 mg, 2.890 mmol), and benzotriazol-1-yloxytris (dimethylamino)-phosphium hexafluorophosphate (639 mg, 1.445 mmol). The mixture is stirred at room temperature for about 4 hours, then poured into 40 mL of brine, and extracted (3×) with ethyl acetate. The combined organic layers are washed with 1N hydrochloric acid (2×, 40 mL), saturated sodium bicarbonate (40 mL) and brine (40 mL). After drying over magnesium sulfate, the mixture is concentrated, and the residue chromatographed on silica gel (9/1 hexanes/ethyl acetate) to give the compound of formula (V) where R$^1$=p-CH$_3$OC$_6$H$_4$ as a white solid: 546 mg, 83% yield, m.p. 116°–118° C. $^1$H NMR (300 MHz, CDCl$_3$): 7.06 (d, J=9.0, 2H), 6.87 (d, J=9.0, 2H), 5.63 (br d, J=9.8, 1H), 5.06 (d, J=9.8, 2H), 3.78 (s, 3H), 1.60 (s, 3H), 1.52 (s, 3H), 1.46 (s, 18H).

(B) 3-Mercapto-D-Valine 4-methoxyphenyl ester trifluoroacetate. To a solution of the product of Example 4(A) (500 mg, 1.098 mmol) in 4 mL of methylene chloride is added 2 mL of anhydrous anisole, and 4 mL of trifluoroacetic acid. After stirring for about 1.5 hours the mixture is concentrated to give 405 mg of the title compound as an off white solid, which is used directly in the next step.

(C) N-Acetyl-3-mercapto-D-valine 4-methoxyphenyl ester. A solution of the product of Example 4(B) (405 mg, 1.097 mmol) in 15 mL of methylene chloride, and triethylamine (222 mg, 2.195 mmol) is cooled in an ice/salt bath. To this mixture is added acetyl chloride (82 mg, 1.0443 mmol) dropwise over about 4 minutes. After stirring about 10 minutes the mixture is poured into water and extracted with methylene chloride (25 mL). The organic phase is washed with 1N hydrochloric acid (15 mL), water (15 mL), dried over magnesium sulfate and concentrated. The residue is chromatographed on silica gel (3/1 hexanes/ethyl acetate) to give the compound of formula (VII) where R$^1$=p-CH$_3$OC$_6$H$_4$, R$^2$=CH$_3$ as an oil: 221 mg, 68% yield. $^1$H NMR (300 MHz, CDCl$_3$): 7.01 (d, J=9.0, 2H), 6.87 (d, J=9.0, 2H), 6.42 (d, J=9.1, 1H), 4.83 (d, J=9.1, 1H), 3.78 (s, 3H), 2.09 (s, 3H), 2.03 (S, 1H), 1.64 (s, 3H), 1.43 (s, 3H).

(D) N-Acetyl-3-(nitrosothio)-D-valine 4-methoxyphenyl ester. To an ice cold solution of the product of Example 4(C) (215 mg, 0.723 mmol) in 8 mL of methylene chloride is added t-butyl nitrite (520 mg, 5.04 mmol). After stirring for about ¾ hours the mixture is concentrated. The residue is chromatographed on silica gel (3/1 hexanes/ethyl acetate) to give N-acetyl-3-(nitrosothio)-D-valine 4-methoxyphenyl ester as a green oil: 185 mg, 78% yield. $^1$H NMR (300 MHz, CDCl$_3$): 6.88 (ABq, J=9.5, 4H), 6.27 (d, J=9.5, 1H), 5.54 (D, J=9.5, 1H), 3.77 (s, 3H), 2.19 (s, 3H), 2.05 (s, 3H), 2.02 (s, 3H).

EXAMPLE 5

N-n-Butyryl-3-(nitrosothio)-D-valine benzyl ester (Formula (I), R$^1$=CH$_2$C$_6$H$_5$, R$^2$=(CH$_2$)$_2$CH$_3$)

This compound is prepared by the same procedure of Example 4 except that an equivalent amount of benzyl alcohol is used in place of 4-methoxyphenol in part (A) and an equivalent amount of n-butyryl chloride is used in place of acetyl chloride in part (C).

EXAMPLE 6

N-Acetyl-3-(nitrosothio)-L-valine 3-chlorophenyl ester (Formula (I), R$^1$=m-ClC$_6$H$_4$, R$^2$=CH$_3$ This compound is prepared by the same procedure of Example 3 except that an equivalent amount of L-penicillamine (i.e., 3-thio-L-valine) is used in place of D-penicillamine in part (A) and an equivalent amount of 3-chlorophenol is used in place of phenol in part (C).

EXAMPLE 7

N-Propionyl-3-(nitrosothio)-L-valine 4-N,N-dimethylaminophenyl ester (Formula (I), R$^1$=p-(CH$_3$)$_2$NC$_6$H$_4$, R$^2$=CH$_2$CH$_3$)

This compound is prepared by the same procedure of Example 3 except that an equivalent amount of L-penicillamine is used in place of D-penicillamine in part (A), 4-N,N-methylamino phenol is used in place of phenol in part (C) and an equivalent amount of n-propionyl chloride is used in place of acetyl chloride in part (E).

EXAMPLE 8

N-(t-Butoxycarbonyl)-3-(nitrosothio)-D-valine 4-methylphenyl ester (Formula (I), $R^1$=p-$CH_3CH_6H_4$, $R^2$=$OC(CH_3)_3$)

This compound is prepared by the same procedure of Example 4 except that an equivalent amount of 4-methylphenol is used in place of 4-methoxyphenyl in part (A) and an equivalent amount of di-t-butyl dicarbonate is used in place of acetyl chloride in part (C).

EXAMPLE 9

N-(Ethoxycarbonyl)-3-(nitrosothio)-D-valine 3-butenyl ester (Formula (I), $R^1$=$C_4H_7$, $R^2$=$OC_2H_5$)

This compound is prepared by the same procedure of Example 4 except that an equivalent amount of 3-buten-1-ol is used in place of 4-methoxyphenyl in part (A) and an equivalent amount of di-ethyl dicarbonate is used in place of acetyl chloride in part (C).

EXAMPLE 10

N-Acetyl-3-(nitrosothio)-D-valine n-butyl ester (Formula (I), $R^1$=n-$C_4H_9$, $R^2$=$CH_3$)

(A) N-Acetyl-3-mercapto-D-valine n-butyl ester. To a solution of N-acetyl-D-penicillamine (2.00 g, 10.46 mmol) in 60 mL of dioxane at 80° C. is added n-butyl-N,N-diisopropyl-pseudourea. The resulting solution is refluxed for about 8 hours. After cooling to room temperature the mixture is diluted with 125 mL of ethyl acetate and filtered. The resulting solution is washed with saturated aqueous sodium bicarbonate, aqueous hydrochloric acid, water, dried over magnesium sulfate, and concentrated. The resulting residue is chromatographed on silica gel (3/1 hexanes/ethyl acetate) to give the compound of formula (IX) where $R^1$=$CH_2CH_2CH_2CH_3$ as an oil: 1375 mg, 53% yield. $^1$H NMR (300 MHz, CDCl$_3$): 6.28 (br d, J=9.5, 1H), 4.62 (d, J=9.5, 1H), 4.13 (t, J=6.6, 2H), 2.05 (S, 3H), 1.95 (S, 1H), 1.66–1.54 (m, 2H), 1.49 (S, 3H), 1.41–1.35 (m, 2H), 1.33 (s, 3H), 0.92 (t, J=7.3, 3H).

(B) N-Acetyl-3-(nitrosothio)-D-valine n-butyl ester. To a ice cold solution of the product of Example 5(A) (120 mg, 0.485 mmol) in 5 mL of methylene chloride is added t-butyl nitrite (350 mg, 3.40 mmol). After stirring for about ½ hours the mixture is concentrated and the residue is chromatographed on silica gel (3/1 hexanes/ethyl acetate) to give N-acetyl-3-(nitrosothio)-D-valine n-butyl ester, the compound of formula (I) where $R^1$=$CH_2CH_2CH_2CH_3$, $R^2$=$CH_3$, as a green oil: 116 mg, 86% yield. $^1$H NMR (300 MHz, CDCl$_3$): 6.37 (brd, J=9.3, 1H), 5.33 (d, J=9.3, 1H), 4.09 (t, J=6.6, 1H), 2.07 (s, 3H), 2.03 (s, 3H), 1.95 (s, 3H), 1.65–1.55 (m, 2H), 1.42–1.29 (m, 2H), 0.925 (t, J=7.3, 3H).

EXAMPLE 11

N-Acetyl-3-(nitrosothio)-D-valine t-butyl ester (Formula (I), $R^1$=t-$C_4H_9$, $R^2$=$CH_3$)

Treatment of N-acetyl-D-penicillamine with t-butyl-N,N-diisopropylpseudourea in an analogous way to that described in Example 5(A), and subsequent treatment of the product with t-butyl nitrite as described in (B) of Example 5 yields the compound of formula (I) where $R^1$=t-$C_4H_9$, $R^2$=$CH_3$ as a green oil. $^1$H NMR (300 MHz, CDCl$_3$): 6.31 (br d, J=9.5, 1H), 5.22 (d, J=9.5, 1H), 2.07 (s, 3H), 2.03 (s, 3H), 1.96 (s, 3H), 1.43 (s, 9H).

EXAMPLE 12

N-Acetyl-3-(nitrosothio)-D-valine n-octyl ester (Formula (I), $R^1$=n-$C_8H_{17}$, $R^2$=$CH_3$)

Treatment of N-acetyl-D-penicillamine with n-octyl-N,N-diisopropylpseudourea in an analogous way to that described in Example 5(A), and subsequent treatment of the product with t-butyl nitrite as described in Example 5(B) yields the compound of Formula (I) where $R^1$=n-$C_8H_{17}$, $R^2$=$CH_3$) as a green oil. $^1$H NMR (300 MHz, CDCl$_3$): 6.23 (br d, J=9.5, 1H), 5.30 (d, J=9.5, 1H), 4.06 (t, J=6.6, 2H), 2.04 (s, 3H), 2.01 (s, 3H), 1.93 (s, 3H), 1.57 (m, 2H), 1.24 (m, 10H), 0.87 (5, J=7.1, 3H).

EXAMPLE 13

N-Acetyl-3-(nitrosothio)-D-valine 2-trimethylsilylethyl ester (Formula (I), $R^1$=$CH_2CH_2SiMe_3$, $R^2$=$CH_3$)

Treatment of N-acetyl-D-penicillamine with 2-trimethylsilylethyl-N,N-diisopropyl-pseudourea in an analogous way to that described in Example 5(A), and subsequent treatment of the product with t-butyl nitrite as described in Example 5(B) yields the compound of formula (I) where $R^1$=$CH_2CH_2SiMe_3$, $R^2$=$CH_3$, as a green oil. $^1$H NMR (300 MHz, CDCl$_3$) 6.27 (br d, J=9.5, 1H), 5.29 (d, J=9.5, 1H), 4.17 (m, 2H), 2.06 (s, 3H), 2.02 (s, 3H), 1.96 (s, 3H), 0.98 (m, 2H), 0.04 (s, 9H).

EXAMPLE 14

N-Acetyl-3-(nitrosothio)-D-valine cyclohexyl ester (Formula (I), $R^1$=$C_6H_{11}$, $R^2$=$CH_3$)

Treatment of N-acetyl-D-penicillamine with cyclohexyl-N,N-diisopropylpseudourea in an analogous way to that described in Example 5(A), and subsequent treatment of the product with t-butyl nitrite as described in Example 5(B) yields the compound of formula (I) where $R^1$=$C_6H_{11}$, $R^2$=$CH_3$, as a green oil. $^1$H NMR (300 MHz, CDCl$_3$): 6.23 (br d, J=9.5, 1H), 5.27 (d, J=9.5, 1H), 4.77 (m, 1H), 2.05 (s, 3H), 2.01 (s, 3H), 1.94 (s, 3H), 1.83–1.22 (m, 10H).

EXAMPLE 15

N-Acetyl-3-(nitrosothio)-D-valine methyl ester (Formula (I), $R^1$=$CH_3$, $R^2$=$CH_3$)

Treatment of N-acetyl-D-penicillamine with methyl-N,N-diisopropylpseudourea in an analogous way to that described in Example 5(A), and subsequent treatment of the product with t-butyl nitrite as described in Example 5(B) yields the compound of formula (I) $R^1$=$CH_3$, $R^2$=$CH_3$ as a green oil. $^1$H NMR (300 MHz, CDCl$_3$): 6.34 (br d, J=9.3, 1H), 5.34 (d, J=9.3, 1H), 3.70 (s, 3H), 2.06 (s, 3H), 2.03 (s, 3H), 1.95 (s, 3H).

We claim:

1. A compound of formula (I)

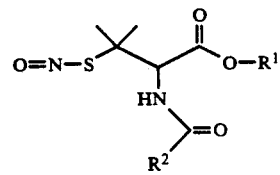

wherein $R^1$ is $C_{1-8}$ alkyl; $C_{5-8}$ cycloalkyl; —($CH_2$)$_n$—Si($CH_3$)$_3$, wherein n is 1 to 5; $C_{2-5}$ alkylenyl; phenyl; naphthyl; or wherein said phenyl or naphthyl bears 1 to 3 substituents independently selected from halogen, amino, $C_{1-8}$ alkyl mono- or disubstituted amino, $C_{1-8}$ alkyl and $C_{1-8}$ alkoxy; and $R^2$ is $C_{1-8}$ alkyl or $C_{1-8}$ alkoxy.

2. A compound of claim 1 wherein $R^1$ is phenyl or phenyl substituted by halogen, $C_{1-8}$ alkyl or $C_{1-8}$ alkoxy.

3. A compound of claim 1 wherein $R^1$ is phenyl or phenyl substituted by halogen, $C_{1-8}$ alkyl or $C_{1-8}$ alkoxy and $R^2$ is methyl.

4. The compound of claim 3 which is N-acetyl-3-(nitrosothio)-D-valine phenyl ester.

5. The compound of claim 1 which is N-acetyl-3-(nitrosothio)-D-valine 4-methoxyphenyl ester.

6. A compound of claim 1 selected from the group:
N-acetyl-3-(nitrosothio)-D-valine n-butyl ester,
N-acetyl-3-(nitrosothio)-D-valine t-butyl ester,
N-acetyl-3-(nitrosothio)-D-valine n-octyl ester,
N-acetyl-3-(nitrosothio)-D-valine 2-trimethylsilylethyl ester,
N-acetyl-3-(nitrosothio)-D-valine cyclohexyl ester and
N-acetyl-3-(nitrosothio)-D-valine methyl ester.

7. A pharmaceutical formulation comprising an effective cardiovascular disorder treating amount of a compound of claim 1.

8. A formulation of claim 7 in the unit dose form of a tablet.

9. A formulation of claim 7 in the form of a transdermal system.

10. The compound N-(t-butoxycarbonyl)-3-(t-butoxycarbonylthio)-D-valine.

* * * * *

UNITED STATES PATENT AND TRADEMARK OFFICE
CERTIFICATE OF CORRECTION

PATENT NO. : 5,187,305
DATED : February 16, 1993
INVENTOR(S) : Thomson et al.

It is certified that error appears in the above-identified patent and that said Letters Patent is hereby corrected as shown below:

On the title page, item (75):

Change inventor's name to --Thomson--.
Item (19) should read--Thomson, et al.--.
Column 2, line 29 change "2-trimethylsilyethyl" to --2-trimethylsilylethyl--.

Column 3, scheme 1, before "step 6" please insert --O-$R^1$--.

Column 5, line 9, change "appreciated" to --appreciate--.

Column 6, line 42, change "faceing" to --facing--.

Column 7, line 67, change "formular" to --formula--.

Column 8, line 18, change "formular" to --formula--.

Column 9, line 50, change "stach" to --starch--.

Column 13, line 4, change "$R^1$p-CH3CH6H4" to --$R^1$=p-CH3C6H4--.

Signed and Sealed this

Twenty-eighth Day of June, 1994

Attest:

BRUCE LEHMAN

*Attesting Officer*  *Commissioner of Patents and Trademarks*